US012674202B2

(12) United States Patent (10) Patent No.: US 12,674,202 B2

Pinard et al. (45) Date of Patent: \*Jul. 7, 2026

(54) METHOD COMBINING IN SITU TARGET AMPLIFICATION AND SPATIAL UNIQUE MOLECULAR IDENTIFIER (SUMI) IDENTIFICATION USING RT-PCR

(71) Applicant: Miltenyi Biotec B.V. & Co. KG, Bergisch Gladbach (DE)

(72) Inventors: Robert Pinard, Bergisch Gladbach (DE); Andreas Bosio, Bergisch Gladbach (DE); Thomas Rothmann, Bergisch Gladbach (DE); Seiyu Hosono, Bergisch Gladbach (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 519 days.

This patent is subject to a terminal disclaimer.

(21) Appl. No.: 18/201,854

(22) Filed: May 25, 2023

(65) Prior Publication Data

US 2023/0383343 A1 Nov. 30, 2023

(30) Foreign Application Priority Data

May 30, 2022 (EP) .................................... 22176171

(51) Int. Cl.
*C12Q 1/6841* (2018.01)
*C12Q 1/686* (2018.01)
*C12Q 1/6874* (2018.01)

(52) U.S. Cl.
CPC ......... *C12Q 1/6874* (2013.01); *C12Q 1/6841* (2013.01); *C12Q 1/686* (2013.01)

(58) Field of Classification Search
CPC .............. C12Q 1/686; C12Q 2525/151; C12Q 2525/155; C12Q 2531/107;

(Continued)

(56) References Cited

U.S. PATENT DOCUMENTS

2020/0354672 A1* 11/2020 Lee ........................ A61K 35/28
2021/0254136 A1 8/2021 Edelman

FOREIGN PATENT DOCUMENTS

EP 0810428 12/1997
EP 1136822 9/2001

(Continued)

OTHER PUBLICATIONS

Mothershed EA, Whitney AM. Nucleic acid-based methods for the detection of bacterial pathogens: present and future considerations for the clinical laboratory. Clin Chim Acta. Jan. 2006;363(1-2):206-20. doi: 10.1016/j.cccn.2005.05.050. Epub Sep. 1, 2005. PMID: 16139259. (Year: 2005).*

(Continued)

*Primary Examiner* — Samuel C Woolwine
*Assistant Examiner* — Kara N Kovach
(74) *Attorney, Agent, or Firm* — Fish & Richardson P.C.

(57) ABSTRACT

Microscopy imaging that allows for multiple mRNAs, proteins and metabolites to be spatially resolved at a subcellular level provides valuable molecular information which is a crucial factor for understanding tissue heterogeneity as for example within the tumor micro environment. The current invention describes a method (High Density-SUMI-Seq) which combines the use of Spatial Unique Molecular Identifier in situ localization and identification (by in situ sequencing or sequential fluorescence hybridization) of rolonies derived from rolling circle amplification of circular oligonucleotides and in vitro sequencing of target amplified RNA or DNA in combination with SUMI identification at a subcellular level with no optical diffraction limitation in the amount of amplified target information that can be analyzed per cell. Apart from amplified RNA or DNA, the High Density-SUMI-Seq method can also be applied using linear (Continued)

oligonucleotides to spatially resolve proteins and metabolites to provide multiomics results.

7 Claims, 6 Drawing Sheets

(58) Field of Classification Search
CPC ........ C12Q 2531/125; C12Q 2563/107; C12Q
2563/179
See application file for complete search history.

(56) References Cited

FOREIGN PATENT DOCUMENTS

| | | |
|----|----|----|
| EP | 1224472 | 7/2002 |
| EP | 1181525 | 7/2003 |
| EP | 3936623 | 1/2022 |
| WO | WO 2017143155 A2 | 8/2017 |
| WO | WO 2018045181 A1 | 3/2018 |

OTHER PUBLICATIONS

Chen et al., "High-throughput mapping of long-range neuronal projection using in situ sequencing," Cell, Oct. 2019, 179(3):772, 35 pages.

Extended European Search Report in European Appln. No. 23175947. 3, mailed on Sep. 15, 2023, 9 pages.

Krishnakumar et al., "A comprehensive assay for targeted multiplex amplification of human DNA sequences," Proceedings of the National Academy of Sciences, Jul. 2008, 105(27):9296-9301.

Lee et al., "Highly multiplexed subcellular RNA sequencing in situ," Science, Mar. 2014, 343(6177):1360-1363.

Lee, "Quantitative approaches for investigating the spatial context of gene expression," Wiley Interdisciplinary Reviews: Systems Biology and Medicine, Mar. 2017, 9(2):e1369, 13 pages.

Payne et al., "In situ genome sequencing resolves DNA sequence and structure in intact biological samples," Science, Feb. 26, 2021;371(6532).eaay3446, 14 pages.

Schneider et al., "Efficient in situ detection of mRNAs using the Chlorella virus DNA ligase for padlock probe ligation," RNA, Feb. 2017, 23(2):250-256.

* cited by examiner

In situ "target capture"

METHOD COMBINING IN SITU TARGET AMPLIFICATION AND SPATIAL UNIQUE MOLECULAR IDENTIFIER (SUMI) IDENTIFICATION USING RT-PCR

CROSS-REFERENCE TO RELATED APPLICATIONS

This application claims the benefit of European Patent Application No. 22176171.1, filed May 30, 2022, the entire contents of which is incorporated herein by reference in its entirety.

FIELD OF INVENTION

The present invention relates to a method for sequencing and in situ localization of rolonies comprising a Spatial Unique Molecular Identifier (SUMI) combined with target capture of RNA or DNA by hybridization and/or amplification from tissue sections for high density spatial analysis by in vitro sequencing. A modification of the sequencing method allows localizing protein and metabolite molecules.

BACKGROUND

Padlock oligonucleotides have proven to be very successful in polymerizing short portion of nucleic acids to which it has been hybridized to. Most padlock approaches begin by reverse transcribing the target into cDNA.

Padlock methods are for example disclosed in "Highly multiplexed subcellular RNA sequencing in situ" by Lee et al., Science. 2014 Mar. 21; 343(6177): 1360-1363. doi: 10.1126/science.1250212 or "Efficient In Situ Detection of mRNAs using the Chlorella virus DNA ligase for Padlock Probe Ligation" by Nils Schneider and Matthias Meier; Feb. 5, 2020—Cold Spring Harbor Laboratory Press.

A comprehensive assay for targeted multiplex amplification of human DNA sequences is published by Sujatha Krishnakumar et al.; PNAS sent for review Feb. 19, 2008.

Further, WO2017143155A2 discloses multiplex alteration of cells using a pooled nucleic acid library and analysis thereof and WO2018045181A1 discloses Methods of generating libraries of nucleic acid sequences for detection via fluorescent in situ sequencing.

The published Padlock methods allow sequencing of DNA or RNA, but do not give any spatial information within a cell and tissue location the sequenced DNA or RNA origins from.

Microscopy imaging that allow for multiple mRNAs to be resolved at a single cell level provides valuable information regarding transcript amount and localization, which is a crucial factor for understanding tissue heterogeneity, the molecular development and treatment of diseases.

Fluorescence in situ hybridization (FISH)-based methods allow for transcripts to be directly labelled in tissue sections and for spatial information to be captured. However, the numbers of probes that can be used is limited and overlap of fluorescence signals is often an issue. Moreover, the optical resolution of confocal microscopy limits often are reached and therefore the amount of probes that can be detected concomitantly is reduced. SeqFISH+, is an sequential fluorescent in situ hybridization approach, that does not use probes already labelled with fluorophores but rather uses transcript-specific ones that contain barcode sequences which serve as target sites for fluorescently labelled secondary probes. The various target-specific probes are identified using secondary probes that bind to these barcode sites during sequential rounds of probing. By limiting the amount of probes that are detected by the secondary probes a limited amount are fluorescing and therefore the signal can be discernible. Multiple separated images are collected and aggregated computationally to create a composite high-resolution image without requiring high resolution instrument microscope.

However, although these approaches allow for the evaluation of several genes simultaneously, the sequence information of the transcript is not captured. Other methods based on single-cell RNA sequencing (scRNA-seq) can profile whole transcriptomes and capture the sequence information. However, the original location at the tissue or single cell level is often also missing. A method where both sequence and spatial information is be captured at a resolution approaching the single-cell remains a difficult challenge. Some approaches have used FISSEQ and BaristaSeq (another gap-filling padlock based approach to achieve that task with a limited read-length of about 15 bases).

Recently in situ genome sequencing (IGS) has been described as a method to simultaneously sequence and image genomes within a sample. This method describes a workflow to localize unique molecular identifiers (UMIs) by short read in situ sequencing followed by amplicon dissociation, PCR and ex situ sequencing of amplicons associated to genomic sequences with UMIs by paired-end sequencing published by A. C. Payne et al., Science 10.1126/science.aay3446 (2020), first online release 31 Dec. 2020.

Very recently a "Method combining targeted RNA or c-DNA in vitro sequencing using padlock oligonucleotides comprising a Spatial Unique Molecular Identifier (SUMI) and in situ sequencing" was described (EP22154712.8). This method describes spatial identification of a target sequence incorporated into the padlock by a combination of in situ sequencing (SUMI) and in vitro sequencing (SUMI and target sequence). As the target sequence and the SUMI sequence are part of the same padlock and the resulting rolony, the density of the target information is limited by the number of rolonies which can be sequenced in situ within the area of a cell. The following invention is overcoming this limitation.

SUMMARY OF THE INVENTION

Object of the invention is a method for obtaining the spatial location and sequence information of a target sequence in at least one RNA or single stranded DNA comprising the steps:

a. hybridizing a first oligonucleotide to a complementary section of the at least one RNA or single stranded DNA wherein the first oligonucleotide is provided with a sequence as first PCR handle;

b. amplifying the first oligonucleotide using the at least one RNA or single stranded DNA as template using reverse transcription-polymerase chain reaction (RT-PCR);

c. removing the at least one RNA or single stranded DNA from the amplified first oligonucleotide;

d. hybridizing a second oligonucleotide to a complementary section of the amplified first oligonucleotide wherein the second oligonucleotide is provided with a sequence as second PCR handle;

e. amplifying the second oligonucleotide using the amplified first oligonucleotide as template using reverse transcription-polymerase chain reaction (RT-PCR)

thereby obtaining a third oligonucleotide comprising sequences as first and second PCR handle and the target sequence;

f. removing the third oligonucleotide from the amplified second oligonucleotide;

g. providing a fourth oligonucleotide at dedicated spatial locations on the sample wherein the fourth oligonucleotide comprises a plurality of concatemers each comprising a sequence complementary to the second PCR handle and at least one sequence as spatial unique molecular identifier (SUMI) comprising at least 2 nucleic acids;

h. determining the sequence of the SUMIs of the fourth oligonucleotides by a first sequencing step to determine the spatial locations of the fourth oligonucleotide, thereby linking the spatial locations with SUMI sequences;

i. hybridizing the third oligonucleotide with the second PCR handle to the complementary sequence of the fourth oligonucleotide;

j. extending the third oligonucleotide with a polymerase using nucleotides complementary to the fourth oligonucleotide as template to thereby incorporating the SUMI into the extended third oligonucleotide;

k. de-hybridizing of the extended third oligonucleotide and determining the sequence of the extended third oligonucleotide by a second sequencing step; and l. linking the sequence information of the extended third oligonucleotide with the information of spatial location obtained in the first sequencing step.

The method of the invention can be further used to obtain the spatial location of proteins or metabolites in a sample. For protein localization the third oligonucleotide includes a barcode-tag next to the first and second PCR handle. The barcode-tag is coding for the protein. The third oligonucleotide is linked to an antibody which is binding to the protein.

5 on the glass flowcell) is sequenced in situ. (B) The target portion of the messenger RNA is amplified directly on a section by proximity ligation probes. (C) The rolonies serve as a template for the generic target capture product and contain the SUMI, the generic sequence 3 of SUMI sequence (2nd) and in this example also contain a restriction site (optional). Thereby the target sequence is extended by the SUMI sequence and can be cleaved in unique monomer. The second PCR handle of the target product (2nd) that is complementary to the rolony generic sequence 5' of SUMI sequence (1st) contained a 3'OH blocking nucleotide (Azido or di-sulfide group) and is extended past the SUMI sequence in situ only after it has been de-protected using a reducing agent such as phosphines. One rolony serves as a template for many target sequences which provides the basis for the High Density (HD) Spatial Unique Molecular Identifier (SUMI) sequencing workflow. The extended target SUMI sequence is amplified by the PCR primers (1st & 2nd) using an highly processive enzyme such Phi29 enzyme (Exponential RCA) as depicted and can be optionally cleave subsequently using a restriction enzyme prior or after it is extracted from the flowcell further processing and amplification by PCR (see FIG. 2 workflow).

Figure 6:
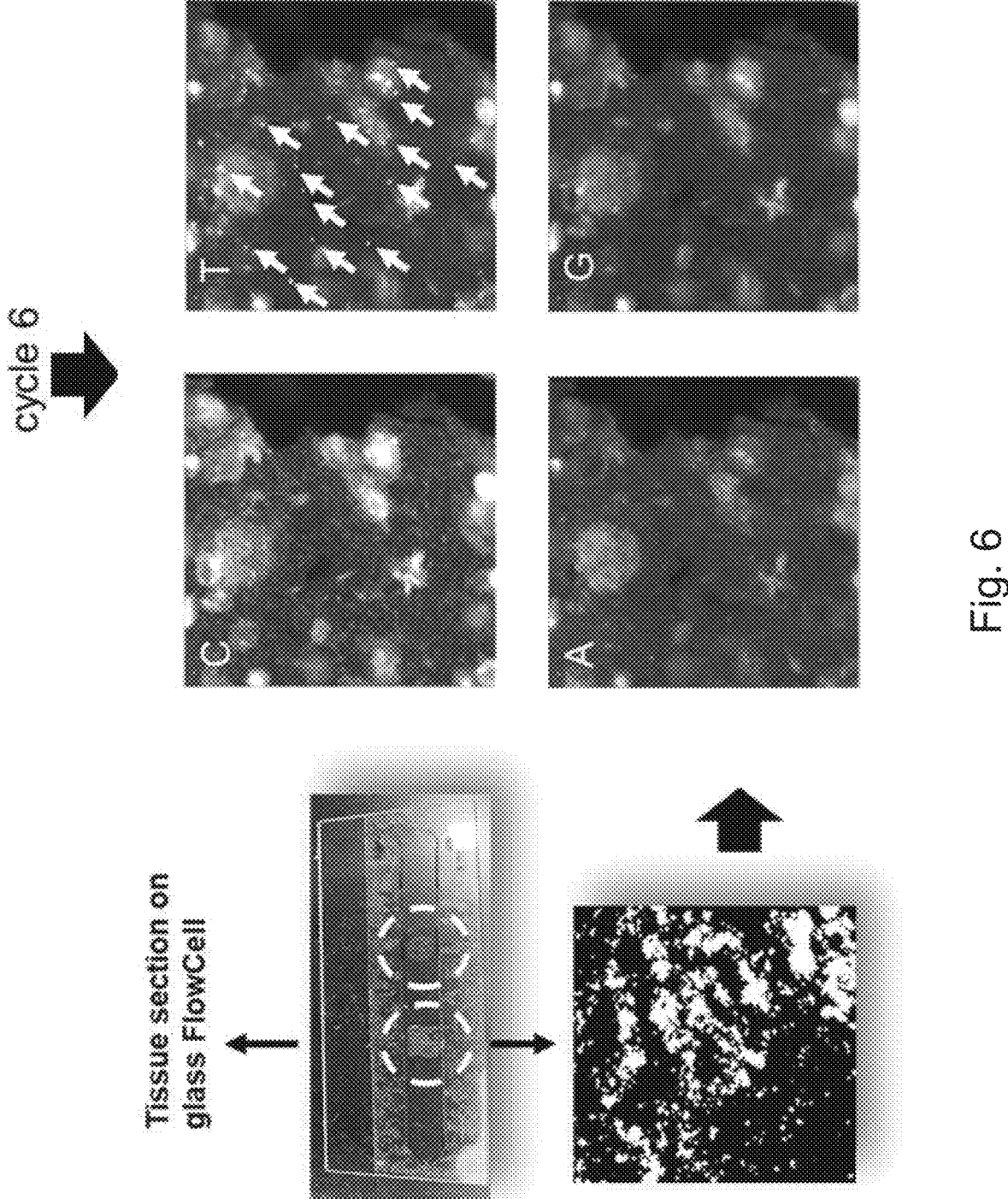

FIG. 6 shows an example of rolonies sequenced in situ, generated from the circular oligonucleotides that can serve as the template for the target-amplified products to be extended by the SUMI sequence. The rolonies are placed on a flowcell and submitted to sequencing by synthesis (SBS). One cycle showing all for fluorescent channels for each of the bases interrogated and the unique incorporation of a T is depicted (cycle 6). After the target amplified products are extended by the SUMI sequence in situ. The SUMI extended target amplified products are removed from the tissue section and are directly subjected to in vitro sequencing.

DETAILED DESCRIPTION

All embodiments and variants of the method to obtain the spatial location and sequence information of a target sequence in a sample comprising at least one RNA or single stranded DNA strand can also be applied in the method for spatial single cell protein expression.

Preferably, the spatial unique molecular identifier (SUMI) comprises 2-500 bp.

The target sequence includes at least the nucleic acids of the hybridized the 3' end of the first oligonucleotide and the hybridized 5' end of the second oligonucleotide as defined in step a and b of the object of the invention for single stranded DNA and RNA target, but may also include the sequence of the region of the oligonucleotides filling the gap after hybridization to the RNA or single stranded DNA.

In a further embodiment of the method, the fourth oligonucleotide may be generated by rolling circle amplification of a circular oligonucleotide. The fourth oligonucleotide may also comprise a sequence allowing the extended third oligonucleotide to be segmented by a restriction enzyme of chemically.

In the present invention, the extended target SUMI sequences may be amplified by a generic PCR reaction before the collection of the extended target SUMI sequences or extended barcode tag SUMI sequences in step f) and before or after determining the spatial location of the rolonies by in situ sequencing or sequential fluorescent in situ hybridization of the SUMI.

As an alternative embodiment to the generic PCR amplification, the extended target SUMI sequence or extended barcode tag SUMI sequence may be part of a padlock probe itself. Here the 5' end and the 3' end of the extended target SUMI sequence or extended barcode tag SUMI sequence would bind to a complementary region 5' and 3' to the SUMI sequence of the SUMI rolony, thereby forming a padlock. After padlock gap fill of the SUMI sequence and ligation, the target sequence would be linked to the SUMI sequence forming a circle. The padlock probes for which the gap has been filled and ligated to form a circular template (the padlock can also be filled but ligated only further in the process) are used to code for the SUMI in the gap fill portion of the padlocks. Finally, the circularized padlock probes may be used as a template for rolling circle amplification (RCA) to generate a DNA strand used for sequencing as defined in.

In the present invention, the workflow can be modified to allow spatial localization by SUMI sequencing for other classes of biomolecules. Here, an oligonucleotide would be linked to the biomolecule binder. The oligonucleotide would contain a sequence (barcode-tag) coding for the binder of the biomolecule (e.g. specific antibody as binder for specific protein). After linking the SUMI sequence with the barcode-tag sequence of the SUMI rolony, followed by in situ and in vitro sequencing spatial multiomics results for the biomolecules linked to the binder will be obtained.

In the present invention before the formation of the rolony as the fourth oligonucleotide can be initiated by an external force (e.g. light or heat) which can be linked to a potential digital pathology imaging process.

In the present invention, the cells may be harvested and subjected to single cell sequencing analysis.

The current invention describes a method overcoming spatial resolution constrains from situ sequencing or sequential in situ hybridization by using SUMI rolonies as a template for spatial localization of target nucleic acids to be identified by in vitro sequencing (SUMI and target).

The method of the invention and its embodiments is further explained referring to the drawings.

Figure 1:
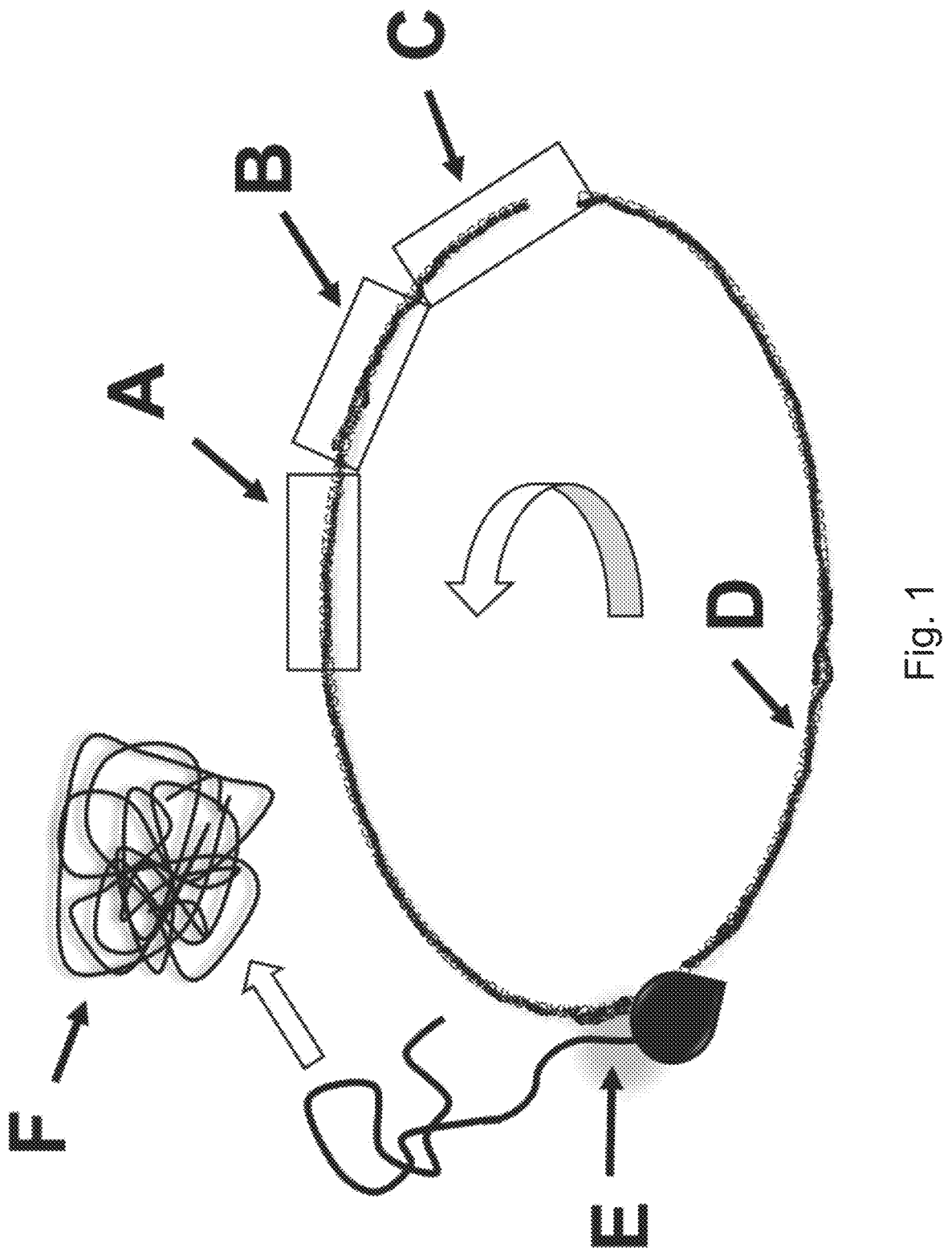
FIG. 1 shows the oligonucleotide design for High Density (HD) Spatial Unique Molecular Identifier (SUMI) sequencing workflow for nucleic acid analysis. (A) Circle first sequence (generic sequence 5' of SUMI sequence). (B) Spatial Unique Molecular Identifier (SUMI) sequence (unique sequence for each circle molecule). (C) Circle second sequence (generic sequence 3' of SUMI sequence). (D) Priming region used for universal rolling circle amplification. (E) Nucleic acid extended by polymerase after initiation of rolling circle amplification. (F) Rolony generated after several rounds of rolling circle amplification.
Figure 4:
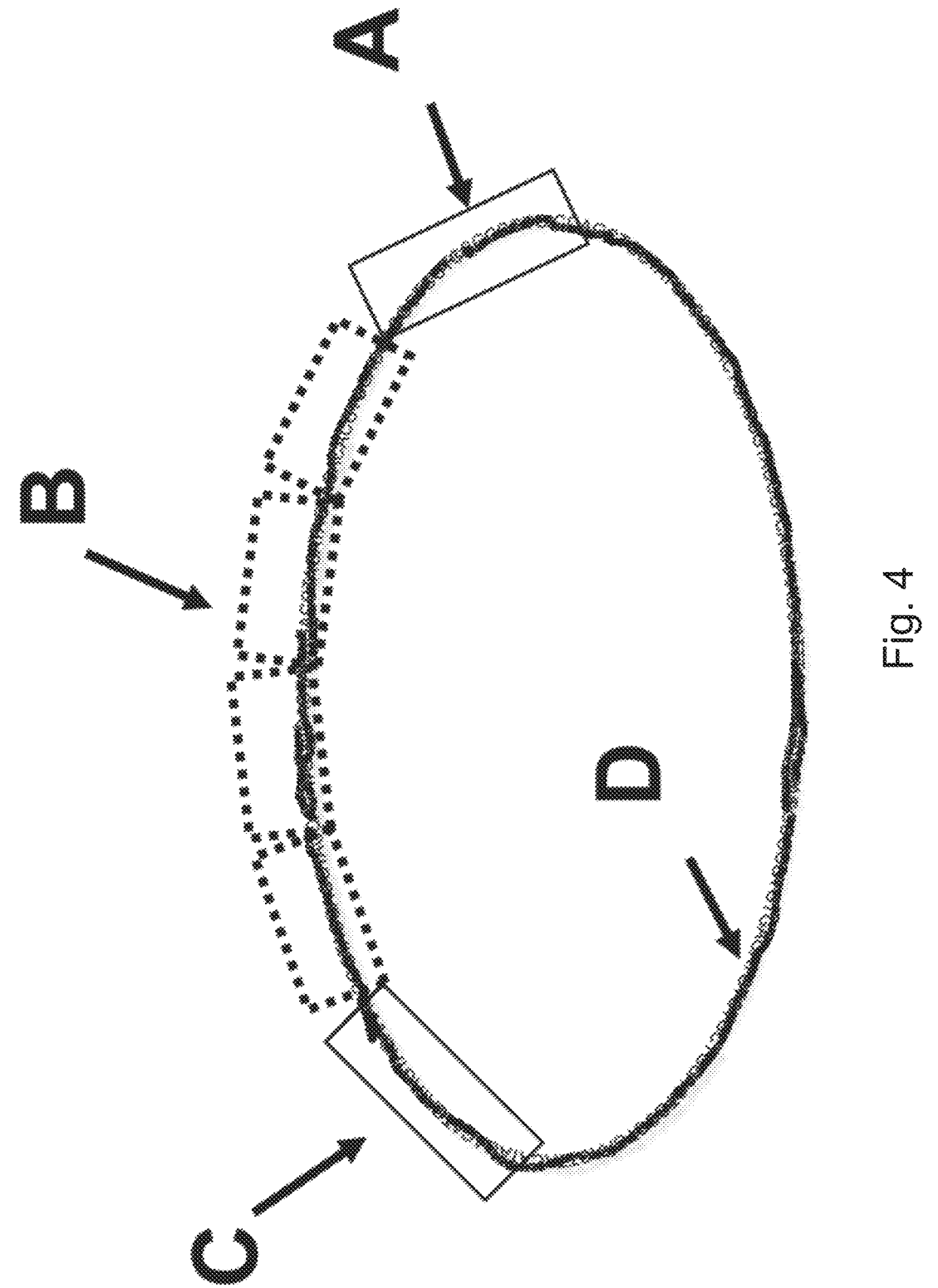
FIG. 4 shows the oligonucleotide design for High Density (HD) Spatial Unique Molecular Identifier (SUMI) hybridization and sequencing workflow for nucleic acid, protein or metabolite analysis. (A) the generic sequence 5' of SUMI sequence (1st). (B) Spatial Unique Molecular Identifier (SUMI) sequence (unique sequence comprised of 4 detection barcode regions as shown here as an example). The 4 barcode regions, each comprising 2-20 nucleotides. The barcode regions may be >4 to increase coding capacity and all barcodes have unique sequences (not shown). (C) the generic sequence 3' of SUMI sequence (2nd) which may also contain a restriction site for monomerization. (D) Priming region used for universal rolling circle amplification.

As shown in FIG. 1 and FIG. 4, the oligonucleotide has one SUMI comprising a minimum of at least two nucleotides. 5' and 3' of the SUMI the circular oligonucleotide comprise generic sequences ($1^{st}$ & 2nd) with 5 to 50 nucleotides. In the method of the invention, the single strand circular template is replicated by a polymerase capable of rolling circle amplification into a plurality of DNA concatemers forming a DNA nanoball or rolony. For this purpose, the oligonucleotide used in the present invention may comprise at least one primer region with 5 to 50 nucleotides for the rolling circle amplification.

In one embodiment of the invention, the generic sequences may not directly follow the SUMI sequences and may be located at variable distance from the SUMI sequence.

In another embodiment of the invention, the primer regions to initiate rolling circle amplification may be identical.

In a further embodiment the oligonucleotide which contains the SUMI may not be circular when provided onto the tissue section, but circularization may happen directly on the tissue.

In one embodiment of the present invention target capture may start with DNA as a target. The respective design adjustments of the linear oligonucleotides needs to be considered.

Figure 3:
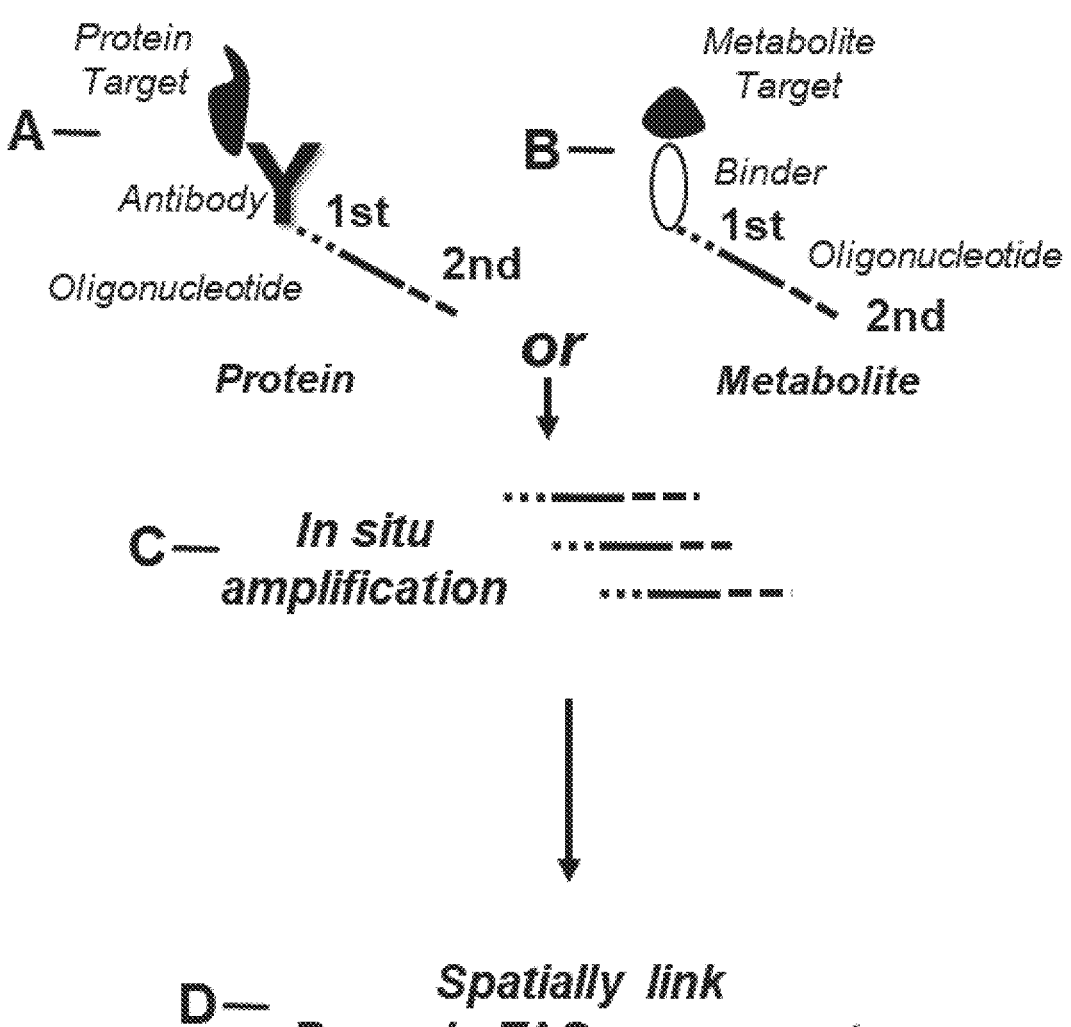
FIG. 3 shows the High Density (HD) Spatial Unique Molecular Identifier (SUMI) sequencing workflow for protein and metabolite analysis. (A) Antibody coupled to oligonucleotide which includes a Barcode-Tag region to identify antibody. (B) Binder coupled to oligonucleotide which includes a Barcode-Tag region to identify the metabolite. (C) Further in situ amplification of the Barcode-Tag sequence is accomplished by the generic PCR handles using the respective generic primers ($1^{st}$ & $2^{nd}$). (D) the barcode TAG sequence is linked to the SUMI sequence as depicted in FIG. 2.

As shown in FIG. 3 the linear oligo may be used to encode for a protein or a metabolite. Also here the 3'-end of the linear oligonucleotide is complimentary to a sequence of the rolony generated from the circular oligonucleotide in order to combine barcode tag and SUMI sequence into one nucleic acid molecule.

In the first embodiment of the invention the circular oligonucleotide which contains a Spatial Unique Molecular Identifier (SUMI) as shown in FIG. 1 is used to generate a rolony on a tissue section. Rolonies serve as sequencing templates for in situ sequencing to identify the Spatial Unique Molecular Identifier (SUMI). The subcellular spatial information for all rolonies are registered and are linked with the SUMI sequence. In situ sequencing may happen before or after in situ target capture.

Figure 2:
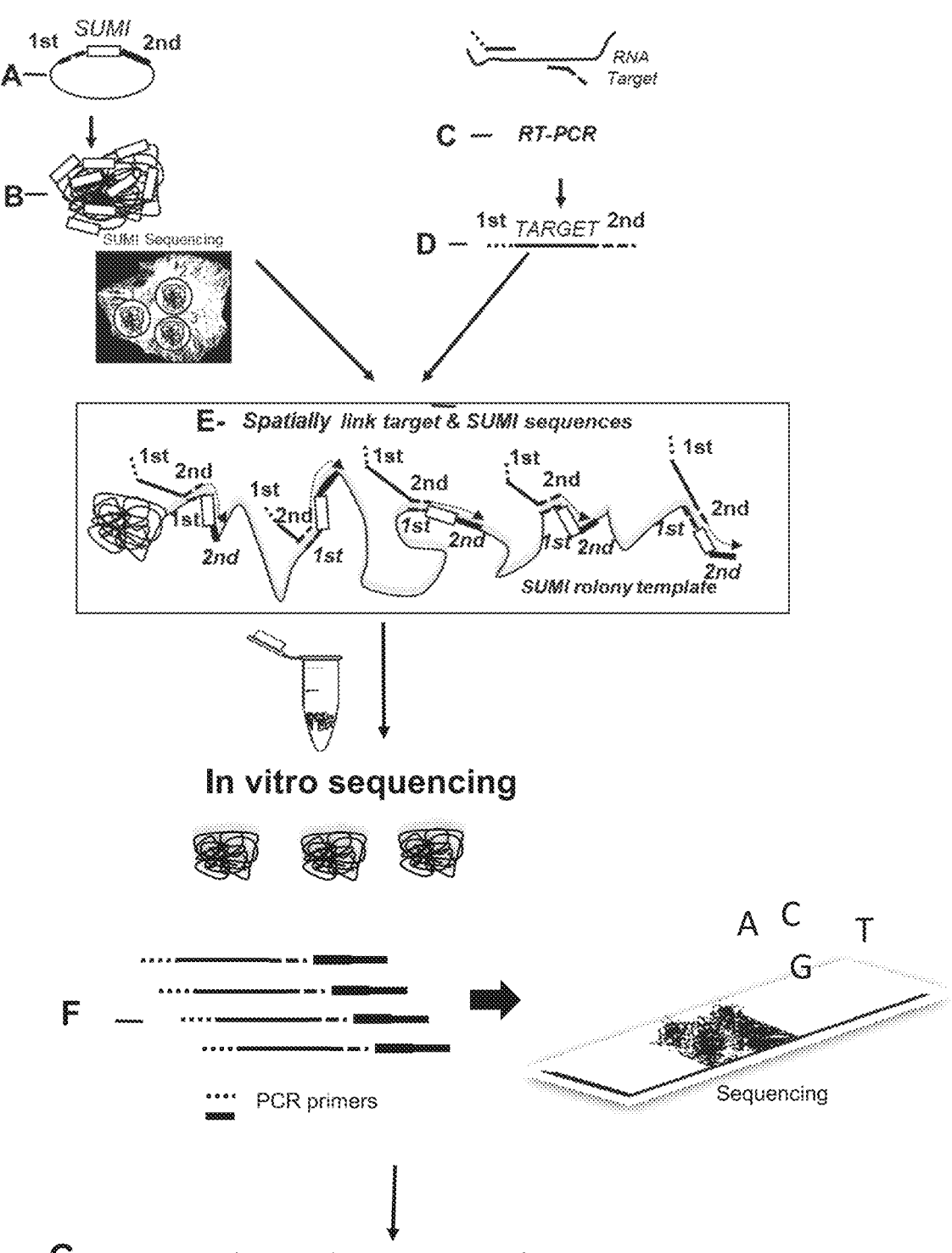
FIG. 2 shows the High Density (HD) Spatial Unique Molecular Identifier (SUMI) sequencing workflow for nucleic acid analysis. (A) SUMI circle nucleic acid templates are added to fixed and permeabilized tissue section. The generic sequence 5' of SUMI sequence (1st) and the generic sequence 3' of SUMI sequence (2nd) and the Spatial Unique Molecular Identifier (SUMI) are all part of the SUMI circle nucleic acid templates. (B) Rolony generated from the SUMI circle nucleic acid templates. The sequence from the SUMI circle nucleic acid template molecules is converted to multiple concatemers of template sequences after rolling circle amplification. The rolonies (circled inside the representation of a cell) are sequenced in situ to derive the SUMI sequence information which is registered spatially (1, 2 and 3 as examples). Note: only a single cell and three SUMI rolonies are shown for illustration. (C) The in situ target capture is performed by targeted RT-PCR reaction where a target-specific pair of oligonucleotides is used directly on a section of tissue that has been fixed and permeabilized to first reverse transcribed and then amplified a specific portion of a messenger RNA. The oligonucleotides contain a primary sequence that binds directly to the target nucleic acid or to its complementary sequence and also a set of sequences generic PCR handles (1st and 2nd) (D) The resulting double-stranded products contain generic PCR handles (1st and 2nd) and the target of interest. Further in situ amplification (if needed) of the target sequence is accomplished by the generic PCR handles labeled first (1st) PCR handle and second PCR handle (2nd). (E) The rolonies serve as a template for the generic target amplified product. Thereby the target sequence product is extended to include and link the SUMI sequence to the target amplified product. In more details, the double-stranded amplified target sequence is denatured in single-strand oligonucleotides and the second (2nd) PCR handle of one of the strand of the amplified target product is hybridized to the complementary rolony generic sequence 5' of SUMI sequence (1st handle). After hybridization to the rolonies, the 3 end of the target amplified product is extended past the SUMI sequence in situ. One rolony serves as a template for many target sequences which provides the basis for the High Density (HD) Spatial Unique Molecular Identifier (SUMI) sequencing workflow. (F) The extended target SUMI sequence is optionally amplified by PCR primers complementary to (1st) and (2nd) handles and eventually removed from the tissue section for further processing in vitro (the optional PCR may also happen in vitro). The extended target SUMI sequence molecule is circularized and amplified to form a rolony in vitro. Rolonies are loaded into the flow cell to serve as templates for in vitro sequencing. The flow cell is loaded into the instrument and in vitro sequencing of the rolonies is performed. (G) The sequence information of the SUMI and the target sequence is obtained (several target sequences may be linked with the same SUMI sequence). The in vivo location of the SUMI sequences and the linked (SUMI sequence-target amplified product) in vitro sequencing are paired to get the spatial location.

The general steps of the invention are shown in FIG. 2. Here, targeted portion of the messenger RNA is amplified directly on a section of tissue that has been fixed and permeabilized. The sequence of interest on the mRNA is amplified using RT-PCR reaction using two specific oligonucleotides targeting directly the messenger RNA wherein the oligonucleotides contain primary sequences that flank the target region to be amplified and a set of generic sequences as PCR handles. Rolonies are generated from the circular oligonucleotides and serve as sequencing templates for in situ sequencing and also as a template for the target-amplified products to be extended by the SUMI sequence. After the target amplified products are extended by the SUMI sequence in situ and the SUMI sequence is determined by in situ sequencing, the SUMI extended target amplified products are removed from the tissue section and are directly subjected to in vitro sequencing. It might be preferable to amplify the SUMI extended target amplified products before circularization, rolonization and in vitro sequencing.

The subcellular location of the target sequence including identified mutations is revealed by linking the target sequence/SUMI obtained in vitro to the SUMI sequence from in situ sequencing. As hundreds of unique SUMI rolonies can spatially be resolved in one cell and each rolony provides thousands of concatemerized SUMI sequences as templates, hundreds of thousands target amplified mRNA sequences can theoretically be spatially identified with subcelluar resolution inside one cell, and therefore providing a High Density (HD) method.

In the second embodiment of the invention the subcellular location of proteins and metabolites will be revealed by the sequencing workflow. The linear oligonucleotide designs as shown in FIG. 3 will use "antigen recognizing moiety" as a binding principle for proteins to determine the subcellular protein location.

The term "antigen recognizing moiety" refers to any kind of antibody or fragmented antibody or fragmented antibody derivatives, directed against markers expressed on the cells of the cell sample. The term relates to fully intact antibodies, fragmented antibody or fragmented antibody derivatives, e.g., Fab, Fab, F(ab)2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificial engineered binding molecules, e.g., peptides or aptamers which target, e.g., cell surface molecules. Such antigen recognizing moieties antibody directed may be against antigen expressed by the biological specimens (target cells) intracellular, like IL2, FoxP3, CD154, or extracellular, like CD3, CD14, CD4, CD8, CD25, CD34, CD56, and CD133.

As a variant to the first embodiment a circular oligonucleotide for a hybridization based SUMI decoding principle for the spatial localization of the rolonies is shown in FIG. 4. In case in situ sequencing of the SUMI cannot be obtained, an hybridization based method may be advantageous. In that case, a multi-color decoding scheme may be used to decode the rolonies. The detection probes used in the method of the present invention may by comprised of oligonucleotide with 2 to 20 nucleotides capable of binding to at least a part of the barcode region. The rolonies generated continue to serve as a template for target capture extension as described before (see FIG. 2). For the High Density (HD) Spatial Unique Molecular Identifier (SUMI) hybridization and sequencing workflow for nucleic acid analysis, a longer sequencing read length is required for in vitro sequencing to decode the SUMI sequence.

In a second embodiment, the method shall be limited to tissue areas of interest. Tissue areas of interest are identified by classical imaging technologies as microscopy. In order to focus the method of in situ sequencing to the areas of interest, the rolony formation shall be controlled by an external force (as light or heat). As rolonies serve as the sequencing template, without rolonies no sequencing will take place. Polymerization and initiation of rolony formation may be inhibited by blocking the polymerase or by blocking the primer. The blocking principle may be removed by an external force as light or heat which can conceptually be directed by the imaging technologies.

As a third embodiment, after SUMI decoding (e.g. by in situ sequencing) the tissue section may be digested and the individual cells are isolated. The rolony containing cells are sorted and eventually subjected to single cell sequencing. Sorting of the rolony containing cells may be accomplished by the increased nucleic acid content as a result of the rolling circle amplification or by fluorescent intensity derived from hybridization probes directed against the rolony sequence. As the SUMI sequence from in situ sequencing may also be identified by single cell sequencing, the information content from single cell sequencing may be linked to the spatial location via the SUMI derived from in situ sequencing.

In this third variant, specific rolonies can be generated from circular oligonucleotides by using specific primers corresponding to targeted gene (FIG. 2) or Barcode-Tag (FIG. 3) of for the targeted antibody or the targeted molecule binder to be recognized for example by the Phi29 enzyme used for RCA allowing for the selective amplification of a subset of amplicons. Finally, the sequenced data are linked back to the area on the tissue where the mRNA or cDNA transcripts or the antibodies or the molecule binders of interest interacted with the circular oligonucleotide originally.

Figure 5:
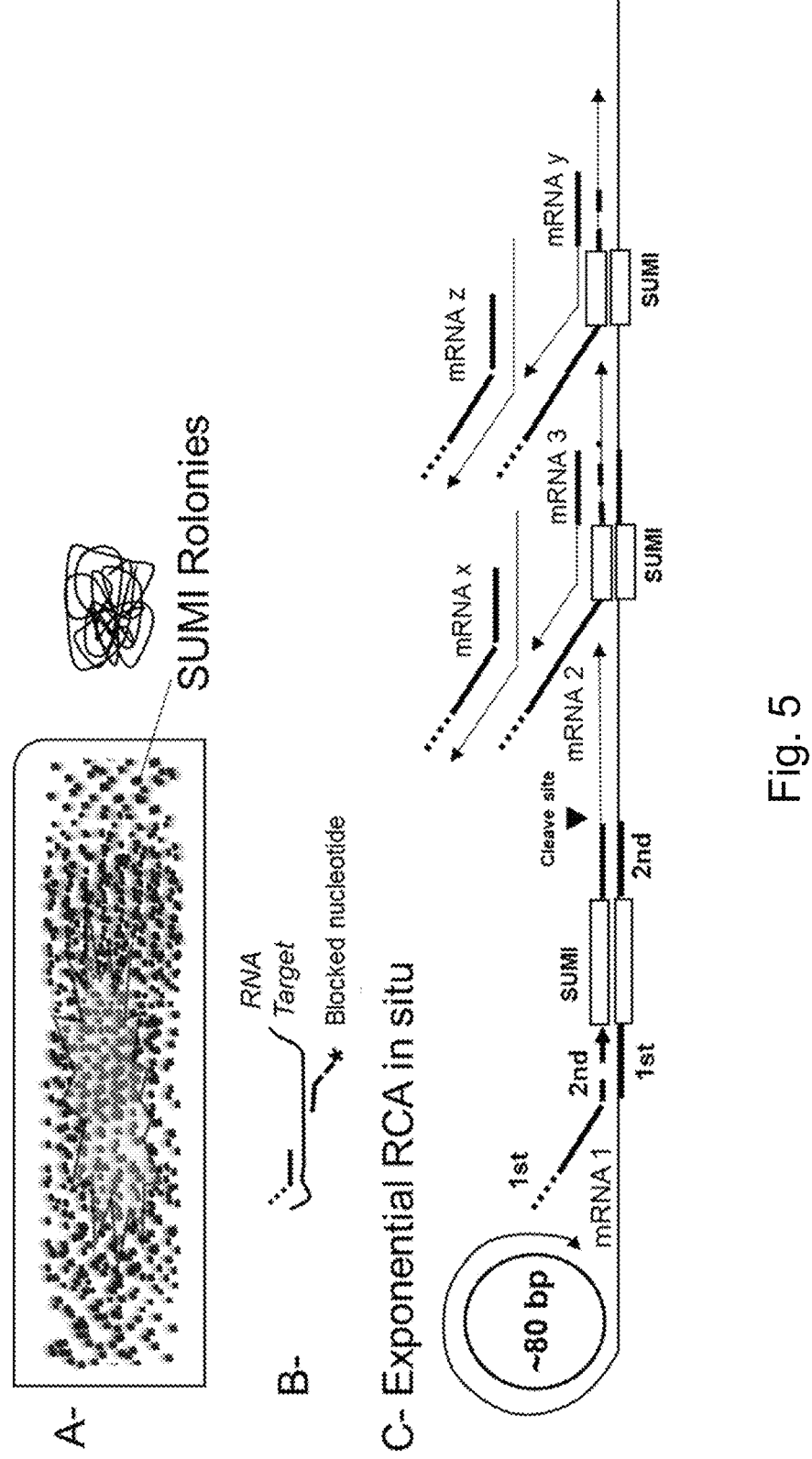
FIG. 5 shows isothermal amplification of SUMI containing amplified probes. (A) The fixed and permeabilized tissue section is placed over SUMI rolonies. The rolony (black dots

In a fourth embodiment, as visualized in FIG. 5, the target SUMI sequence is established and also amplified by Exponential RCA using a highly processive polymerase such as Phi29. Here also, the rolonies serve as a template for the generic target capture product and contain the SUMI. One rolony may serve as a template for many target sequences which provides the basis for the High Density (HD) Spatial Unique Molecular Identifier (SUMI) sequencing workflow.

Samples to be analysed with the disclosed method may originate from any specimen, like whole animals, organs, tissues slices, cell aggregates, or single cells of invertebrates, (e.g., Caenorhabditis elegans, Drosophila melanogaster), vertebrates (e.g., Danio rerio, Xenopus laevis) and mammalians (e.g., Mus musculus, Homo sapiens). A biological sample may have the form of a tissues slice, cell aggregate, suspension cells, or adherent cells. The cells may be living or dead.

The spatial information of the rolonies i.e. the location of the rolonies on the sample is determined for example by an imaging step. In yet another variant of the method according to the invention, the sample is converted into isolated cells which are then immobilized by trapping in microcavities or by adherence.

Imaging may be performed for example with techniques are known as "Multi Epitope Ligand Cartography", "Chip-based Cytometry" or "Multiomics", described for example, in EP 0810428, EP1181525, EP 1136822 or EP1224472. In this technology, cells are immobilized and contacted with antibodies coupled to fluorescent moiety. The antibodies are recognized by the respective antigens on the biological specimen (for example on a cell surface) and after removing the unbound marker and exciting the fluorescent moieties, the location of the antigen is detected by the fluorescence emission of the fluorescent moieties. In certain variants, instead of antibodies coupled to fluorescent moieties, anti-bodies coupled to moieties detectable for MALDI-Imaging or CyTOF can be used. The person skilled in the art is aware how to modify the technique based on fluorescent moiety to work with these detection moieties. The location of the target moieties is achieved by a digital imaging device with a sufficient resolution and sensitivity in for the wavelength of the fluorescence radiation. The digital imaging device may be used with or without optical enlargement for example with a fluorescence microscope. The resulting images are stored on an appropriate storing device like a hard drive, for example in RAW, TIF, JPEG, or HDF5 format.

What is claimed is:

1. A method for obtaining the spatial location and sequence information of at least one target nucleic acid sequence in a sample comprising the steps:
   a. hybridizing a first oligonucleotide to a complementary section of the at least one target nucleic acid sequence wherein the first oligonucleotide is provided with a sequence as first PCR handle;
   b. amplifying the first oligonucleotide using the at least one target nucleic acid sequence as a template using reverse transcription-polymerase chain reaction (RT-PCR);
   c. removing the at least one target nucleic acid sequence from the amplified first oligonucleotide;
   d. hybridizing a second oligonucleotide to a complementary section of the amplified first oligonucleotide wherein the second oligonucleotide is provided with a sequence as second PCR handle;
   e. amplifying the second oligonucleotide using the amplified first oligonucleotide as template using reverse transcription-polymerase chain reaction (RT-PCR) thereby obtaining a third oligonucleotide comprising sequences as first and second PCR handle and the target sequence;
   f. removing the third oligonucleotide from the amplified second oligonucleotide;
   g. providing a fourth oligonucleotide at dedicated spatial locations on the sample wherein the fourth oligonucleotide comprises a plurality of concatemers each comprising a sequence complementary to the second PCR handle and at least one sequence as spatial unique molecular identifier (SUMI) comprising at least 2 nucleotides;
   h. determining the sequence of the SUMIs of the fourth oligonucleotides by a first sequencing step to determine the spatial locations of the fourth oligonucleotide, thereby linking the spatial locations with SUMI sequences;
   i. hybridizing the third oligonucleotide with the second PCR handle to the complementary sequence of the fourth oligonucleotide;
   j. extending the third oligonucleotide with a polymerase using nucleotides complementary to the fourth oligonucleotide as template to thereby incorporating the SUMI into the extended third oligonucleotide;
   k. de-hybridizing of the extended third oligonucleotide and determining the sequence of the extended third oligonucleotide by a second sequencing step; and
   l. linking the sequence information of the extended third oligonucleotide with the information of spatial location obtained in the first sequencing step.

2. The method of claim 1 characterized in that the fourth oligonucleotide comprises further a sequence allowing the extended third oligonucleotide to be segmented by a restriction enzyme or chemically.

3. The method of claim 1 characterized in that the fourth oligonucleotide is provided by rolling circle amplification of a circular oligonucleotide comprising a sequence complementary to the second PCR handle and at least one sequence as spatial unique molecular identifier (SUMI).

4. The method of claim 3 characterized in that the rolling circle amplification (RCA) is activated by light and/or heat.

5. The method of claim 1 characterized in that the first sequencing step is performed after incorporating the SUMI sequence into the extended third oligonucleotide.

6. The method of claim 1 characterized in that the sample comprises at least one cell, wherein the at least one cell is further subjected to single cell sequencing.

7. The method of claim 1 characterized in that the sample comprises at least one cell, wherein the at least one cell is subjected to in situ sequencing followed by single cell sequencing.

* * * * *